(12) United States Patent
Kovi et al.

(10) Patent No.: US 11,332,495 B2
(45) Date of Patent: May 17, 2022

(54) PROCESS FOR THE PREPARATION OF DEGARELIX ACETATE AND DEGARELIX ACETATE-MANNITOL PREMIX

(71) Applicant: RK Pharma Solutions LLC, Piscataway, NJ (US)

(72) Inventors: Ravishanker Kovi, Monroe Township, NJ (US); Jayaraman Kannappan, Vadodara (IN); Sai Saisuryanarayana Donthukurthi, Gujarat (IN); Shivam Saroj, Anand (IN); Piyush Fadadu, Vadodara (IN); Srikrishna Apar, Aurangabad (IN); Sandeep Aher, Aurangabad (IN); Veerabhadra Rao Bobbili, Vadodara (IN)

(73) Assignee: RK PHARMA SOLUTIONS LLC, Piscataway, NJ (US)

( * ) Notice: Subject to any disclaimer, the term of this patent is extended or adjusted under 35 U.S.C. 154(b) by 0 days.

(21) Appl. No.: 17/020,983

(22) Filed: Sep. 15, 2020

(65) Prior Publication Data
US 2021/0094984 A1    Apr. 1, 2021

(30) Foreign Application Priority Data

Sep. 21, 2019   (IN) .............................. 201921038164
Feb. 28, 2020   (IN) .............................. 202021008664

(51) Int. Cl.
  *C07K 7/06*      (2006.01)
  *C07K 1/04*      (2006.01)
  *C07K 1/06*      (2006.01)

(52) U.S. Cl.
  CPC ................. *C07K 7/06* (2013.01); *C07K 1/04* (2013.01); *C07K 1/061* (2013.01)

(58) Field of Classification Search
  CPC .. C07K 7/06; C07K 1/04; C07K 1/061; Y02P 20/55
  See application file for complete search history.

(56) References Cited

U.S. PATENT DOCUMENTS 8,828,938 B2    9/2014  Zhang

FOREIGN PATENT DOCUMENTS

| CN | 102952174 A | 3/2013 | |
| CN | 102329373 A | 10/2014 | |
| WO | WO1997034923 A1 | 9/1997 | |
| WO | WO1998046634 A1 | 10/1998 | |
| WO | WO1999026964 A1 | 6/1999 | |
| WO | WO-2011066386 A1 * | 6/2011 | ............... C07K 7/23 |
| WO | WO2011066386 A1 | 6/2011 | |

OTHER PUBLICATIONS

Noshita et al (Organic Letters, 2016, 18, 6062-6065) (Year: 2016).*
Firmagon Document from FDA, 2015, 1-18. (Year: 2015).*

* cited by examiner

*Primary Examiner* — Sudhakar Katakam
(74) *Attorney, Agent, or Firm* — Antonio Papageorgiou; Lombard & Geliebter LLP

(57) ABSTRACT

Methods for preparing degarelix acetate are provided that include the steps of providing a suitable resin; deprotecting the resin with a diethylenetriamine solution; reacting sequentially the deprotected resin with different Fmoc protected amino acids; deprotecting the amino acid in each sequence with a diethylenetriamine solution in a stepwise fashion to yield a degarelix crude compound; and purifying the degarelix crude compound to yield pharmaceutically acceptable degarelix acetate. Methods of preparing degarelix acetate-mannitol premix and the resulting degarelix acetate-mannitol premix are also provided.

10 Claims, 3 Drawing Sheets

PROCESS FOR THE PREPARATION OF DEGARELIX ACETATE AND DEGARELIX ACETATE-MANNITOL PREMIX

BACKGROUND

The present application relates to the field of peptide molecule, and more particularly to methods of solid phase synthesis of Degarelix acetate of formula I and use of this compound in the preparation of Degarelix-Mannitol premix formulation. Specifically, the present application relates to improved processes for the preparation of Degarelix acetate and Degarelix-Mannitol premix. The present application also relates to the use of this formulated product in the treatment of various disease.

Prostate cancer is a leading cause of morbidity and mortality for men in the world. Degarelix, also known as FE200486, is a third generation gonadotropin releasing hormone (GnRH) receptor antagonist (a GnRH blacker) that has been developed and approved for prostate cancer patients in need of androgen ablation therapy (Doehn et al., Drugs 2006, vol. 9, No. 8, pp. 565-571; WO 1998046634).

Degarelix acetate (also called FIRMAGON) D-Alaninamide, N-acetyl-3-(2-naphthalenyl)-D-alanyl-4-chloro-Dphenylalanyl-3-(3-pyridinyl)-D-alanyl-L-seryl-4-[[[(4S)-hexahydro-2,6-dioxo-4-pyrimidinyl]carbonyl]amino]-L phenylalanyl-4-[(aminocarbonyl)amino]-D-phenylalanyl-L leucyl-N6-(1-methylethyl)-L-lysyl-L-prolyl. It has an empirical formula of $C_{82}H_{103}N_{18}O_{16}Cl$ and a molecular weight of 1632.3 Da. Firmagon powder for injection contains degarelix, which is a GnRH receptor antagonist, as the acetate salt. Degarelix acetate has the structural formula I shown in Table A.

Firmagon is available as 80 mg and 120 mg lyophilized powder for subcutaneous injection. Each Firmagon lyophilized powder contains equivalent to 120 mg of degarelix for the starting dose, and 80 mg of degarelix for the maintenance dose. The 80 mg vial contains 200 mg mannitol and the 120 mg vial contains 150 mg mannitol. Firmagon is supplied as a powder to be reconstituted with Sterile Water for Injection ("WFI") or, depending on the degarelix dose and concentration, with mannitol solution (e.g. 2.5% or 5%) in order to maintain isotonicity.

Firmagon is indicated for treatment of patients with advanced prostate cancer. Degarelix acts by immediate and competitive blockade of GnRH receptors in the pituitary and, like other GnRH antagonists, does not cause an initial stimulation of luteinizing hormone production via the hypothalamic-pituitary-gonadal axis, and therefore does not cause testosterone surge or clinical flare. Degarelix is administered as a subcutaneous injection in the abdominal region only.

There are several methods for peptide synthesis. A solid-phase peptide synthesis (SPPS), which has been a widely preferred method for producing large quantities of peptides. Another developed and commonly used approach for peptide synthesis is liquid-phase peptide synthesis (LPPS).

The solid phase synthesis of peptides has been known. The general principle of this type of synthesis is as follows:

An N-protected amino acid (the protecting group Boc or F-moc) is attached to a solid, non-soluble support (commonly a polystyrene resin) at its carboxylic end via a linking group. The N-protecting group is removed by means which do not detach the amino acid from the solid support, and a second N-protected amino acid is coupled to the one already attached (commonly by use of a carbodi-imide coupling

TABLE A

Formula I

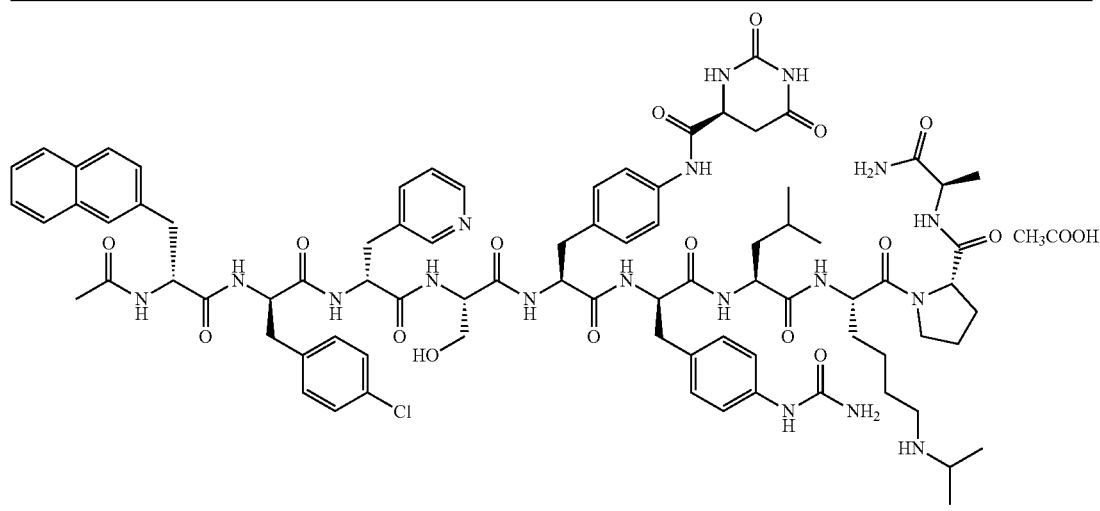

Degarelix was approved by the FDA on 24 Dec. 2008, and by EMEA on 27 Feb. 2009. Degarelix acetate is a sterile lyophilized powder for injection containing degarelix (as the acetate) and mannitol. Degarelix is a synthetic linear decapeptide amide containing seven unnatural amino acids, five of which are D-amino acids. The acetate salt of degarelix is a white to off-white amorphous powder of low density as obtained after lyophilization.

agent). The sequence is repeated using as many N-protected amino acids as are required until the desired peptide has been formed, still attached at its carboxyl end to the solid support. The final N-protecting group is removed and the peptide is separated from the solid support by cleavage of the linking group (commonly by use of a strong acid).

Degarelix was first discussed in WO 1998046634, which is incorporated herein by reference, which also discusses the synthesis and use of Degarelix as GnRH receptor antagonist agents. WO 1998046634, which is incorporated herein by reference, reported a method for synthesis of degarelix by using Boc as a protecting group, the Boc-D-Ala-OH coupled with MBHA resin, and then washed, to remove the Boc protecting group with an acid, connected to a next amino acid sequence, wherein the side chain of 4 Aph 5 and 6 using Fmoc protection and deprotection with piperidine/dimethylformamide (DMF) solution, and then were added L-Hor Cbm group and a side chain.

Further WO 2011066386, which is also incorporated herein by reference, also employed Boc solid-phase synthesis method. WO 2011066386 discusses the process by using protection with boc group, but since the bit Boc protecting groups hinders its hydrophobicity, resulting in acidolysis of degarelix. The removal of the protective group is carried out under acidic conditions (tifluroacetic acid-TFA). While effective to avoid the generation of Ac-D-2NaI-D-Phe (4Cl)-D-3Pal-Ser-Aph (Z) -D-4Aph (Cbm) -Leu-ILys-Pro-D-Ala-$NH_2$ is but ultimately Boc strategy to use HF cleavage, have a greater harm to the environment.

U.S. Pat. No. 8,828,938, which is also incorporated herein by reference, discusses a method for synthesis of degarelix acetate by using Fmoc solid phase synthesis. Amino acid 5 and 6 respectively Fmoc-Aph (L-hor)-OH and Fmoc-Aph (tBuCbm)-OH are used for coupling. According to the literature, 5 hydrogenated orotic acid fragment 4-amino phenylalanine side chain is unstable in an alkaline environment, prone to rearrangement by products structure hydantoin. the amino acids are deprotected by using piperidine.

CN 102329373 and CN102952174, which are also incorporated herein by reference, further discuss the process for the preparation of degarelix using Fmoc strategy of solid-phase synthesis method, which is 4-amino-5-phenylalanine side chain with trityl (trt) or allyloxycarbonyl (alloc) first protected decapeptide After then, removed protecting groups plus Hor. Trt protecting group on the side chains with TFA removed the need, in the course of removal of the acid, Boc protecting group on the side chain ILys off easily, in addition, the peptide linker and the resin is easily broken when it is treated with TFA.

WO 1997034923 and WO 1999026964, incorporated herein by reference, discuss the liquid phase processes for the preparation of biologically active peptides. WO 1999026964 in particular discusses liquid phase synthesis of decapeptides having activity as GnRH antagonists. Application no. WO 1999026964 describes a liquid phase process which involves first preparing the central peptide fragments of the 5 and 6 positions of a decapeptide with the side chains fully elaborated and then assembling the peptide through a "4-2-4", "3-3-4" or "3-4-3" fragment assembly pattern.

The prior processes for the preparation Degarelix acetate of formula I suffer serious drawbacks, such as higher industrial time with low yield, purities and tedious process, e.g., for lyophilisation. Prior processes also use of hazardous reagents for synthesis of degarelix, which is not good for environment.

The present application describes improved industrial scale process for the preparation of degarelix acetate with better yield and/or purity. The present application further provides preparation of degarelix acetate active pharmaceutical ingredient (API) and use thereof in the preparation of Degarelix acetate-mannitol premix formulation. The present application also discloses use of this formulation in the treatment of various ailments, e.g., advanced prostate cancer.

SUMMARY

In a first embodiment, the present application provides process for the preparation of Degarelix acetate of formula I. To solve the above technical problems, the technical scheme adopted herein is as follows:

In general, Fmoc-Rink amide AM resin may be de-protected, e.g., with diethylenetriamine in DMF, to get Rink amide AM resin. Rink amide AM resin stepwise undergoes acid amine coupling with respective Fmoc protected amino acid to get degarelix crude compound. In each step, Fmoc protected amine may be de-protected using diethylenetriamine to get a respective free amine. The obtained crude degarelix acetate may then be further purified and converted to pharmaceutically acceptable salts, preferably to degarelix acetate.

An object according to at least one embodiment disclosed in the present application is to solve the aforementioned problems of in the art, to provide mild reaction conditions, easy operation, safety, low environmental pollution, high-yield, high-quality, and/or large-scale production for degarelix solid phase synthesis methods.

In a second embodiment, the present application provides a process for the preparation of Degarelix acetate-mannitol sterile premix, which involves one or more of the following steps: Dissolving a non-sterile degarelix acetate in suitable solvent, Adding a non-sterile mannitol in above solution, Performing an aseptic filtration, Adding anti-solvent in solution (step c), and Isolation of Degarelix-acetate sterile premix.

An object according to this embodiment of the present application is to solve the aforementioned problems of the available formulation via making an easy operation, less environmental pollution, less time, high-quality, and/or large-scale production with safety for degarelix-mannitol sterile premix.

In a third embodiment, the present application provides the use of this formulated Degarelix acetate-mannitol sterile premix in the treatment of various types of diseases, including cancer and more specifically prostate cancer.

Accordingly, this application provides the improved process for the preparation of Degarelix acetate by using diethylenetriamine base for deprotection to get more yield with better purity of degarelix acetate and use of this Degarelix acetate in preparation of Degarelix acetate-mannitol premix formulation.

In at least aspect, a method or methods for preparing degarelix acetate are provided that include the steps of providing a suitable resin; deprotecting the resin with a diethylenetriamine solution; reacting sequentially the deprotected resin with different Fmoc protected amino acids ;deprotecting the amino acid in each sequence with a diethylenetriamine solution in a stepwise fashion to yield a degarelix crude compound; and purifying the degarelix crude compound to yield pharmaceutically acceptable degarelix acetate.

In at least one embodiment, the resin comprises Fmoc-Rink amide AM resin.

In at least one embodiment, the resin comprises an amine protected resin.

In at least one embodiment, the diethylenetriamine solution comprises diethylenetriamine in DMF.

In at least one embodiment, the diethylenetriamine solution comprises 5% diethylenetriamine in DMF.

In at least one embodiment, deprotecting the resin in a stepwise fashion comprises: activating the amine protected resin to obtain an N terminal protected resin and conjugating the N terminal protected resin with amino acid to obtain an amino acid coupled resin.

In at least one embodiment, the method further includes condensing remaining amino acids and coupling the remaining amino acids to a preceding coupling thereof sequentially according to the order from C-terminus to N-terminus of the amino acid sequence of degarelix to obtain resin attached crude degarelix.

In at least one embodiment, the method further includes deprotecting the resin attached crude degarelix to obtain the crude degarelix.

In at least one embodiment, the resin attached crude degarelix is deprotected using an acidic deprotecting agent.

In at least one embodiment, the acidic deprotecting agent is at least one agent selected from a group consisting of tifluroacetic acid (TFA), hydrochloric acid (HCl), and methanesulfomc acid.

In at least one embodiment, the method further includes drying the crude degarelix and wherein the crude degarelix has a purity of at least 85%.

In at least one embodiment, the method further includes purifying the crude degarelix.

In at least one embodiment, the step of condensing comprises using at least one condensing agent selected from a group consisting of N,N-diisopropyl carbodiimide (DIPC), Benzotriazol-1-yloxy)tripyrrolidinophosphonium hexafluorophosphate (PyBOP), and N,N-dicyclohexyl carbodiimide (DCC).

In at least one embodiment, the Fmoc protected amino acids comprises a plurality selected from the group consisting of D-alanine, proline, lysine, leucine, 4-amino-phenylaniline, 4-L-hyroortoyl-4-aminophenylalanine, t-butyl serine, 3-pyridylalanine, 4-chlorophenylalanine, 2-napthylalanine.

In another aspect, a degarelix acetate-mannitol premix is provided.

In at least one embodiment, the degarelix acetate-mannitol premix contains Degarelix acetate obtained using the methods disclosed herein.

In another aspect, a method or methods for preparing a degarelix acetate sterile premix are provided that includes the steps of dissolving degarelix acetate in a suitable solvent; adding a mannitol solution to the degarelix acetate solution; aseptically filtering the mixture and adding an anti-solvent; and isolating therefrom degarelix-acetate sterile premix.

In at least one embodiment, the solvent comprises at least one of dimethyl sulfoxide (DMSO), dimethylformamide (DMF), dimethylacetamide (DMA) N-metyl pyrrolidone (NMP), and Dimethylformamide (DMF).

In at least one embodiment, the anti-solvent comprises at least one of acetone, methyl tert-butyl ether (MTBE), ethyl acetate, isobutyl acetate, isopropyl acetate, diisopropyl ether (DIPE), and tetrahydrofuran (THF).

BRIEF DESCRIPTION OF THE DRAWINGS

For the purposes of illustration, drawings are presently preferred, it being understood, however, that the invention is not limited to the precise embodiments shown.

DETAILED DESCRIPTION

Figure 1:
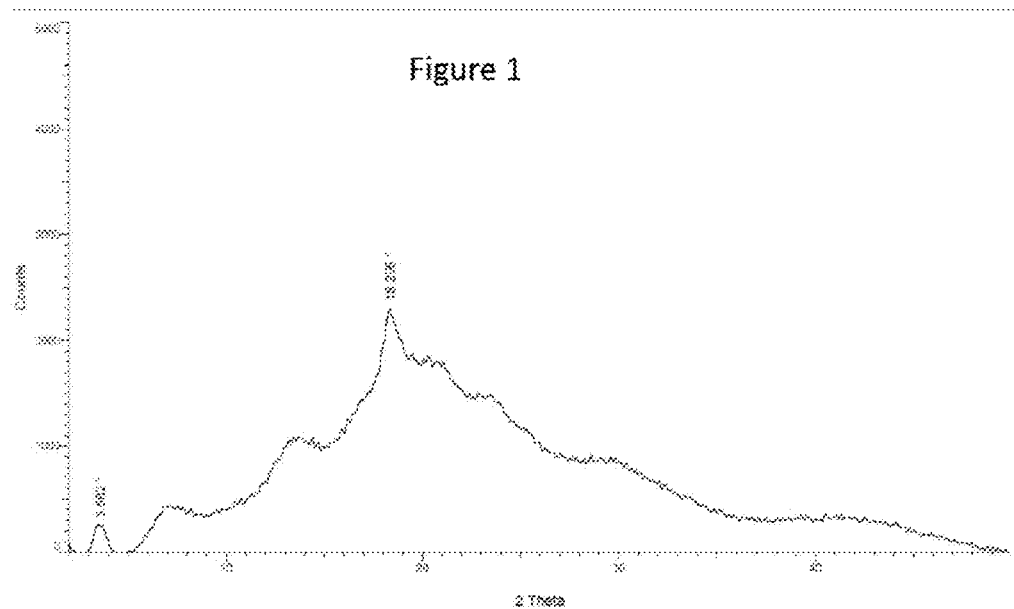
FIG. 1 illustrative a characteristic X-ray powder diffraction (XRD) pattern of Degarelix acetate.

Embodiments of the present application now will be described more fully hereinafter with reference to the accompanying examples and experiments, in which illustrative embodiments of the application are shown. The inventions herein may, however, be embodied in many different forms and should not be construed as limited to the embodiments set forth herein; rather, these embodiments are provided so that this disclosure will be thorough and complete, and will fully convey the scope of the invention to those skilled in the art. Well-known functions or constructions may not be described in detail for brevity and/or clarity.

The terminology used herein is for the purpose of describing particular embodiments only and is not intended to be limiting. As used herein, the singular forms "a", "an" and "the" are intended to include the plural forms as well, unless the context clearly indicates otherwise. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All percentages and ratios used herein are by weight of the total composition and all measurements made are at 25° C. and normal pressure unless otherwise designated. All temperatures are in degrees Celsius unless specified otherwise.

As used herein, "comprising" means the elements recited, or their equivalent in structure or function, plus any other element or elements which are not recited. The terms "having" and "including" are also to be construed as open ended unless the context suggests otherwise.

All ranges recited herein include the endpoints, including those that recite a range "between" two values.

Important aspects in the preparation of Degarelix acetate are quality and production costs of the end product. Owing to regulatory requirements, high quality standards have to be met. Of interest in this context are purity and content of the active compound. Coupled to purity, it is in particular the spectrum of by-products which need to be monitored. Minor components have to be toxicologically qualified and assessed. Accordingly, they are listed in specifications and the maximum occurrence in the product is defined. For reasons of product safety and for the good of the patient, the by-product spectrum and the presence of individual contaminants are kept as low as possible to achieve the desire result.

Degarelix has 10 amino acid backbone, composed to give the following sequence:

Ac-D-2Nal-D-Phe(4Cl)-D-3Pal-Ser-4Aph(Hor)-D-4Aph (Cbm)-Leu-ILys-Pro-D-Ala-$NH_2$.

Amino acid side chains in the present process may be protected using conventional protecting group on the amino acid side chain. Generally, amino group of amino acid may be protected using Boc protecting group or are protected by Fmoc protecting group. In the present application, amino group may be protected by Fmoc. Amino acid protected in the preparation of Degarelix include Fmoc-Pro, Fmoc-Lys (iPr, Boc), Fmoc-Leu, Fmoc-D-Aph (Cbm), Fmoc-Aph (Hor), Fmoc-Ser (tBu), Fmoc -D-Pal, Fmoc-D-Cpa and Fmoc -D-Nal.

To solve the drawback of know prior process, the present application provides the following technical solutions:

A synthetic method of degarelix production involves the activation of amine protected resin in a first step. N terminal protected resin may then be conjugated with D-alanine via esterification reaction by using a condensing agent and an activating reagent to obtain the peptide resin I.

Figure 4:
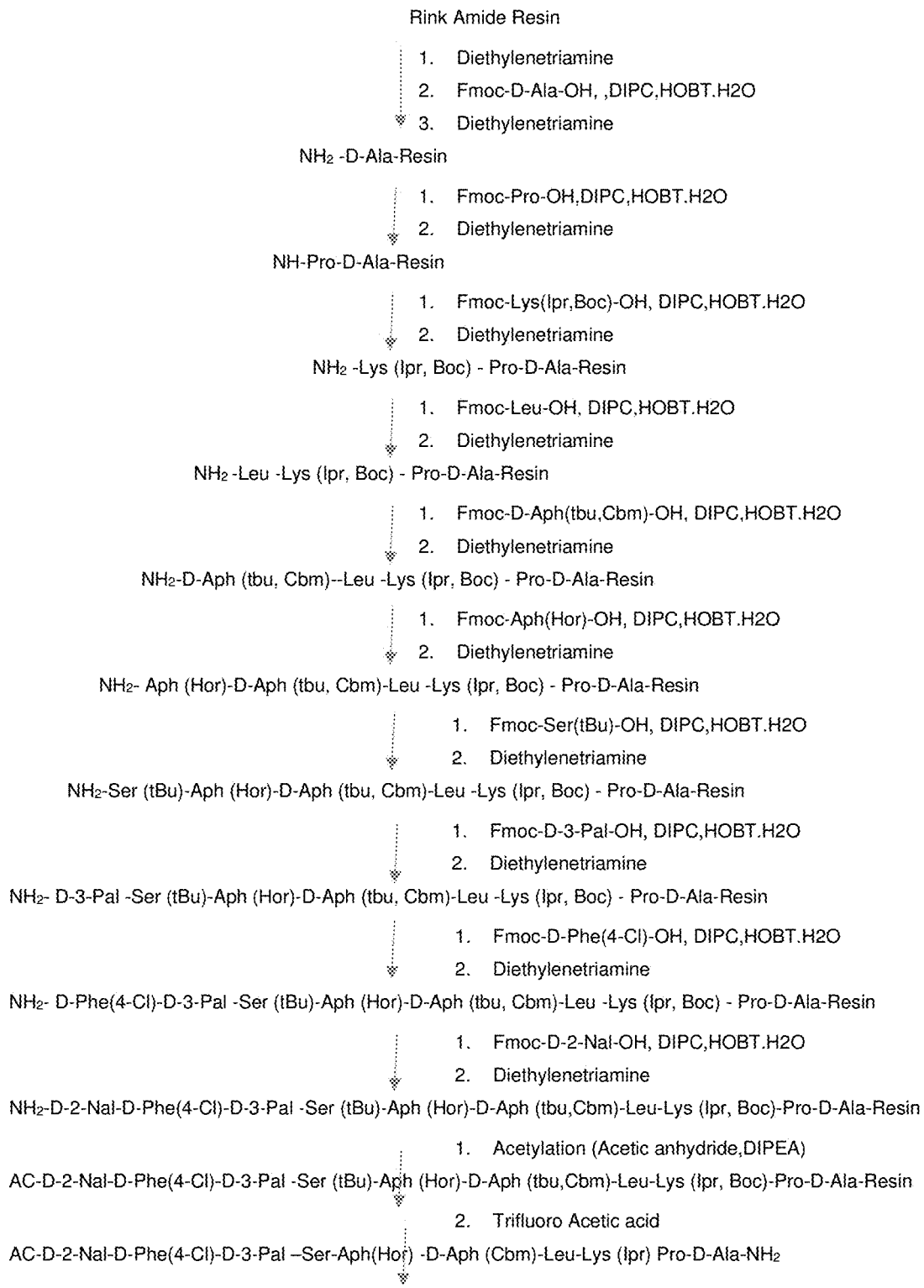
FIG. 4 is a flow diagram for the production of Degarelix acetate according to one embodiment disclosed herein.

A schematic representation of the improved process for the production of degarelix is depicted in FIG. 4.

The extending and coupling in the present application means that after the coupling of the first amino acid with amino resin, the rest amino acids are condensed (condensation between the main chain amino group and carboxyl group) and coupled with the preceding one coupled amino acid sequentially according to the order from C-terminus to N-terminus of the amino acid sequence of degarelix. During the coupling disclosed in the present application, the molar ratio of the protected amino acid to the corresponding peptide resin during each extending and coupling is preferably increased as amino acid numbers are increased.

The acid hydrolysis is performed by using a deprotecting agent.

Once all ten amino acid is coupled then acetylation reaction is carried out to get resin attached crude degarelix. This resin containing crude degarelix may then be deprotected with acidic deprotecting agent to get crude degarelix.

Resin used in the synthesis of degarelix is not limited to rink amide AM resin, rink amide resin, rink MBHA resin or sieber resin. Preferably, rink amide resin is used.

Rink amide resin has the structural formula shown in Table B, wherein the line on the left represents polystyrene resin:

TABLE B

Rink Amide Resin

I

II

TABLE B-continued

Rink Amide Resin

III

IV

V

Suitable condensing agent includes, but is not limited to, N,N-diisopropyl carbodiimide (DIPC), Benzotriazol-1- yloxy)tripyrrolidinophosphonium hexafluorophosphate (PyBOP), N,N-dicyclohexyl carbodiimide (DCC).

Coupling agents used in the particular reaction may be selected from O-(1-benzotriazolyl)-N,N,N',N'-tetramethyluronium hexafluorophosphate (HBTU), O-(7-aza-1-benzotriazolyl)-N,N,N',N'-tetramethyluronium hexafluorophosphate (HATU) and O-benzotriazole-N,N,N',N'-four tetrafluoroborate a solution of methyl urea (TBTU).

Organic bases used in synthesis may be selected from N-methylmorpholine (NMM), piperidine, diethylenetriamine (DET), N,N-diisopropylethylamine (DIPEA), triethylenetetramine (TETA), tetraethylenepentamine (TEPA), aminoethylethanolamine (AEEA), aminoethylpiperazine (AEP) or triethylamine (TEA) and more preferably diethylenetriamine (DET).

Acidic deprotecting used for the deprotection resin may be selected from tifluroacetic acid (TFA), hydrochloric acid (HCI), or methanesulfomc acid for t-butyl ether containing resin as a protecting group, more preferably trifluroacetic acid (TFA).

Suitable solvents which can be used for the preparation of compound degarelix includes tetrahydrofuran (THF), dimethyl sulfoxide (DMSO), dimethylformamide (DMF), dimethylacetamide (DMA) and the like; any mixtures of two or more thereof. Preferably, DMF is used as the solvent.

A suitable temperature for the reaction may be about 0° to about 80° C., preferably between 20° C. to 60° C., or more preferably about 30° C. to 40° C., or any other suitable temperatures. The reaction may be carried out for any desired time period ranging from about 10 minutes to about 24 hours or longer.

The isolation of crude product may be induced by using techniques known including, but not limited to, concentrating, cooling, separation, stirring, shaking, combining with an anti-solvent, adding seed crystals, evaporation, flash evaporation, simple evaporation, rotational drying, or the like.

The crude that is obtained may carry a small proportion of occluded mother liquor containing a higher percentage of impurities and, if desired, the crude may be washed with a solvent to wash out the mother liquor. Evaporation as used herein refers to distilling of solvent almost completely at atmospheric pressure or under reduced pressure. Flash evaporation as used herein refers to distilling of solvent by using a technique includes but is not limited to tray drying, fluidized bed drying. The recovery of intermediate can be done by decantation, centrifugation, gravity filtration, suction filtration and like.

In another aspect, the present application relates to the purification of Degarelix. The purification can be carried out in various ways, e.g., by preparative-HPLC.

Figure 2:
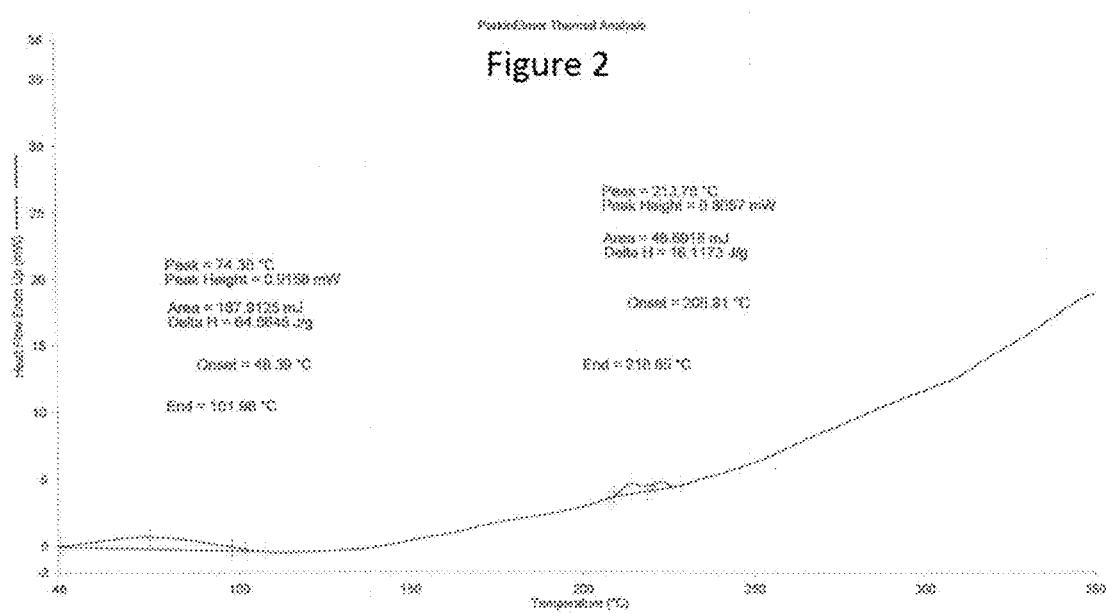
FIG. 2 is a graphical depiction of a characteristic differential scanning calorimetry (DSC) pattern of Degarelix acetate.
Figure 3:
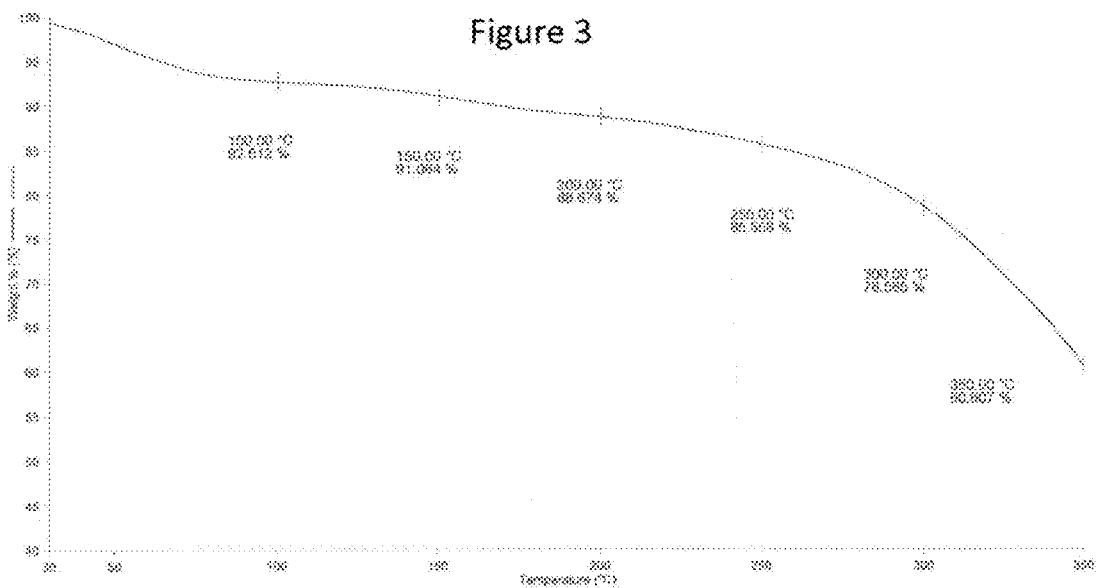
FIG. 3 is a graphical depiction of a characteristic thermogravimetric analysis (TGA) pattern of Degarelix acetate.

Once the desired purification performed by prep-HPLC is achieved, the obtained solution containing degarelix acetate is placed under reduced temperature and pressure to obtain the powder of Degarelix acetate. XRD, DSC and TGA analysis of obtained Degarelix acetate is depicted in FIGS. 1, 2 and 3.

The Degarelix acetate synthesized by this route has advantageous properties including at least one of: chemical purity, absence of closed impurity, stability—such as storage stability, stability to dehydration, stability to polymorphic conversion, flowability, solubility, morphology or crystal habit, low hygroscopicity and low content of residual solvents.

In a second embodiment, the present application provides the process for the preparation of Degarelix acetate-mannitol sterile premix.

The process generally involves the steps of:
a. Dissolving a non-sterile degarelix acetate in suitable solvent,
b. Adding a non-sterile mannitol in above solution,
c. Performing an aseptic filtration,
d. Adding anti-solvent in solution (step c) and
e. Isolation of Degarelix-acetate sterile premix.

Dissolving a solution in step a) includes: 1) direct use of a reaction mixture containing degarelix acetate, this is obtained in the course of its synthesis; or 2) direct use of reaction mixture containing degarelix acetate that is obtained after purification; or 3) dissolving crude degarelix acetate in a solvent.

Any physical form of degarelix acetate may be utilized in step (a) of the process embodiments herein above.

Suitable solvents which can be used for the dissolving degarelix acetate includes dimethyl sulfoxide (DMSO), dimethylformamide (DMF), dimethylacetamide (DMA) N-metyl pyrrolidone (NMP), Dimethylformamide (DMF) any mixtures of two or more thereof. Preferably DMSO.

Step (b) involves the addition non-sterile mannitol in above filtered solution. The addition can be done as single time charge or lot wise addition.

The solution obtained in step (b) may then undergo aseptic filtration. Suitable techniques to remove insoluble particles are filtration, micron filter, centrifugation, decantation, and any other techniques known in the art. The solution can be filtered by passing through paper, or other membrane material, or a clarifying agent such as celite. Depending upon the equipment used and the concentration and temperature of the solution, the filtration apparatus may need to be preheated to avoid premature precipitation of solid.

Step (d) involves the addition of anti-solvent in above reaction mass. Suitable solvents which can be used as anti-solvent includes acetone , methyl tert-butyl ether (MTBE), ethyl acetate, isobutyl acetate, isopropyl acetate, diisopropyl ether (DIPE), tetrahydrofuran(THF), ethanol and the like; any mixtures of two or more thereof.

Step (e) involves the isolation of Degarelix acetatemannitol sterile premix. The isolation of product may be induced by using techniques which include but are not limited to concentrating, cooling, separation, stirring, shaking, filtration, adding seed crystals, evaporation, flash evaporation, simple evaporation, rotational drying, or the like. In a particular application, filtration is performed to get Degarelix acetate-mannitol sterile premix.

In another aspect present application involves recovery of Degarelix acetate-mannitol sterile premix after removal of solvent. The recovery can be done by using known processes. The resulting solid may be collected by using techniques such as by scraping, or by shaking the container, or other techniques specific to the equipment used. The isolated solid may be optionally be further dried to afford Degarelix acetate-mannitol sterile premix.

The resulting compound may be optionally further dried. Drying can be carried out in a tray dryer, vacuum oven, air oven, buchi®, rotavapor®, cone vacuum dryer, rotary vacuum dryer, fluidized bed dryer, spin flash dryer, flash dryer, gravity oven, or the like. The drying can be carried out at temperatures of less than about 60° C., less than about 40° C., less than about 30° C., or any other suitable temperatures; at atmospheric pressure or under a reduced pressure; as long as the Degarelix acetate-mannitol sterile premix is not degraded in its quality. The drying can be carried out for any desired times until the required product quality is achieved. Suitable time for drying can vary from few minutes to several hours for example from about 30 minutes to about 24 or more hours.

Once obtained, Degarelix acetate-mannitol sterile premix may be used as the nucleating agent or "seed" crystals for subsequent crystallizations of Degarelix acetate-mannitol sterile premix from solutions.

A process is performed at suitable temperature for any of the above step (a) to (d), may be about 0° to about 80° C., preferably between 20° C. to 60° C., or preferably about 30° C. to 40° C., or any other suitable temperatures. The reaction may be carried out for any desired time period ranging from about 10 minutes to about 24 hours or longer.

The Degarelix acetate-mannitol sterile premix obtained by this process have advantageous properties such as at least one of: chemical purity, stability—such as storage stability, stability to dehydration, stability to polymorphic conversion, flowability, solubility, morphology or crystal habit, low hygroscopicity and low content of residual solvents.

In a third embodiment, the present application provides the use of this formulated Degarelix acetate-mannitol sterile premix in the treatment of various type of disease.

The Degarelix acetate-mannitol sterile premix may be reconstituted with sterile water for Injection, USP before administration in patient. The reconstituted product may then used for treating prostate cancer.

Certain specific aspects and embodiments of the present application will be explained in more detail with reference to the following examples, which are provided only for purposes of illustration and should not be construed as limiting the scope of the present application in any manner.

Experimental Section

Experiments are divided into two parts:
A. Preparation of Degarelix acetate and
B. Preparation of Degarelix acetate-Mannitol premix
A. Preparation of Degarelix Acetate
Step 1 Rink Amide Resin Activation Fmoc-Rink amide AM resin (0.5 g) was placed in a peptide vessel and the resin was washed with 5 ml DMF 2 times and kept in DMF (5 ml) for 45 min and the solvent was then removed by applying vacuum. The washed resin was then deprotected with 5% diethylenetriamine in DMF 5 ml for 15 min. The vessel was emptied by applying vacuum and treated with 5% diethylenetriamine in DMF (5 ml) for 15 min. The vessel was emptied by applying vacuum and the resin was washed with DMF (5 ml). The vessel was further washed with methanol (5 ml*2 times) and DMF (5 ml*2 times). A solution of 0.326 gm Fmoc-Ala-OH (3.0 eq), 0.14 gm HOBT.H$_2$O (3.0 eq) and 0.165 ml diisopropylcarbodimide (3.0 eq) was dissolved in DMF at 0-10° C. and allowed to activate for 10 min. This solution was charged into the peptide vessel, stirred for 2 hrs. and deprotected with 5% diethylenetriamine in DMF (5 ml) for 15 min. The vessel was emptied by applying vacuum and a second treatment 5% diethylenetriamine in DMF 5 ml for 15 min. The vessel was emptied by applying vacuum and the resin was washed with DMF (5 ml). The vessel was further washed with methanol (5 ml*2 times) and DMF (5 ml*2 times).
Step 2

A solution of 0.354 gm Fmoc-Pro-OH (3.0 eq), 0.14 gm HOBT.H$_2$O (3.0 eq) and 0.165 ml diisopropylcarbodimide (3.0 eq) was dissolved in DMF at 0-10° C. and allowed to activate for 10 min. This solution was then charged into the peptide vessel, stirred for 2 hrs. and washed with 5 ml DMF (4 times). Then it was deprotected with 5% diethylenetriamine in DMF 5 ml for 15 min. The vessel was emptied by applying vacuum and a second treatment 5% diethylenetriamine in DMF 5 ml for 15 min. The vessel was emptied by applied vacuum and the resin washed with DMF (5 ml). The vessel was further washed with methanol (5 ml*2 times) and DMF (5 ml*2 times).
Step 3

A solution of 0.536 gm Fmoc-Lys (ipr,Boc)-OH (3.0 eq), 0.14 gm HOBT.H$_2$O (3.0 eq) and 0.165 ml diisopropylcarbodimide (3.0 eq) was dissolved in DMF at 0-10° C. and allowed to activate for 10 min and this solution charged into peptide vessel , stirred for 2 hrs., and washed with 5 ml DMF 4 times, and deprotected with 5% diethylenetriamine in DMF 5 ml for 15 min. The vessel was emptied by applying a vacuum and a second treatment 5% diethylenetriamine in DMF 5 ml for 15 min. The vessel was emptied by applied vacuum and the resin washed with DMF (5 ml). The vessel was further washed with methanol (5 ml*2 times) and DMF (5 ml*2 times).
Step 4

A solution of 0.371 gm Fmoc-Leu-OH (3.0 eq), 0.14 gm HOBT.H$_2$O (3.0 eq) and 0.165 ml diisopropylcarbodimide (3.0 eq) was dissolved in DMF at 0-10° C. and allowed to activate for 10 min and this solution charged into a peptide vessel, stirred for 2 hrs., washed with 5 ml DMF 4 times, and deprotected with 5% diethylenetriamine in DMF 5 ml for 15 min. The vessel was emptied by applying a vacuum and second treatment 5% diethylenetriamine in DMF 5 ml for 15 min. The vessel was emptied by applied vacuum and resin washed with DMF (5 ml). The vessel was further washed with methanol (5 ml*2 times) and DMF (5 ml*2 times).
Step 5

A solution of 0.351 gm Fmoc-DAph(tBuCbm)-OH (2.0 eq),0.107 gm HOBT.H$_2$O (2.0 eq) and 0.11 ml diisopropylcarbodimide (2.0 eq) was dissolved in DMF at 0-10° C. and allowed to activate for 10 min and this solution charged into the peptide vessel, stirred for 2 hrs., washed with 5 ml DMF 4 times, and deprotected with 5% diethylenetriamine in DMF 5 ml for 15 min. The vessel was emptied by applying a vacuum and a second treatment of 5% diethylenetriamine in DMF 5 ml for 15 min. The vessel was emptied by applying a vacuum and the resin washed with DMF (5 ml). the vessel was further washed with methanol (5 ml*2 times) and DMF (5 ml*2 times).
Step 6

A solution of 0.379 gm Fmoc-Aph(Hor)-OH (2.0 eq), 0.107 gm HOBT.H$_2$O (2.0 eq) and 0.11 ml diisopropylcarbodimide (2.0 eq) was dissolved in DMF at 0-10° C. and allowed to activate for 10 min and this solution charged into the peptide vessel, stirred for 2 hrs. and deprotected with 5% diethylenetriamine in DMF 5 ml for 15 min. The vessel was emptied by applying a vacuum and a second treatment 5% diethylenetriamine in DMF 5 ml for 15 min. The vessel was emptied by applying a vacuum and the resin washed with DMF (5 ml). The vessel was further washed with methanol (5 ml*2 times) and DMF (5 ml*2 times).
Step 7

A solution of 0.402 gm Fmoc-Ser(tBu)-OH (3.0 eq),0.14 gm HOBT.H$_2$O (3.0eq) and 0.165 ml diisopropylcarbodimide (3.0 eq) was dissolved in DMF at 0-10° C. and allowed to activate for 10 min and this solution charged into peptide vessel, stirred for 2 hrs., washed with 5 ml DMF 4 times, and deprotected with 5% diethylenetriamine in DMF 5 ml for 15 min. The vessel was emptied by applying a vacuum and a second treatment 5% diethylenetriamine in DMF 5 ml for 15 min. The vessel was emptied by applying a vacuum and the resin washed with DMF (5 ml). The vessel was further washed with methanol (5 ml*2 times) and DMF (5 ml*2 times).

Step 8

A solution of 0.407 gm Fmoc-D-3-Pal-OH (3.0 eq), 0.14 gm HOBT.H$_2$O (3.0 eq) and 0.165 ml diisopropylcarbodimide (3.0 eq) was dissolved in DMF at 0-10° C. and allowed to activate for 10 min and this solution charged into peptide vessel, stirred for 2 hrs., and washed with 5 ml DMF 4 times and deprotected with 5% diethylenetriamine in DMF 5 ml for 15 min. The vessel was emptied by applying a vacuum and a second treatment 5% diethylenetriamine in DMF 5 ml for 15 min. The vessel was emptied by applying a vacuum and the resin washed with DMF (5 ml). A vessel was further washed with methanol (5 ml*2 times) and DMF (5 ml*2 times).

Step 9

A solution of 0.442 gm Fmoc-D-Phe (4-Cl)-OH (3.0 eq), 0.14 gm HOBT.H$_2$O (3.0eq) and 0.165 ml diisopropylcarbodimide (3.0 eq) was dissolved in DMF at 0-10° C. and allowed to activate for 10 min and this solution charged in to peptide vessel, stirred for 2 hrs. washed with 5 ml DMF 4 times, and deprotected with 5% diethylenetriamine in DMF 5 ml for 15 min. The vessel was emptied by applying a vacuum and a second treatment 5% diethylenetriamine in DMF 5 ml for 15 min. The vessel was emptied by applying a vacuum and the resin washed with DMF (5 ml). The vessel was further washed with methanol (5 ml*2 times) and DMF (5 ml*2 times).

Step 10

A solution of 0.459 gm Fmoc-D-2-Nal-OH (3.0 eq), 0.14 gm HOBT.H$_2$O (3.0 eq) and 0.165 ml diisopropylcarbodimide (3.0 eq) was dissolved in DMF at 0-10° C. and allowed to activate for 10 min and this solution charged into peptide vessel, stirred for 2 hrs., washed with 5 ml DMF 4 times, and deprotected with 5% diethylenetriamine in DMF 5 ml for 15 min. The vessel was emptied by applying a vacuum and second treatment 5% diethylenetriamine in DMF 5 ml for 15 min. The vessel was emptied by applying a vacuum and resin washed with DMF (5 ml). A vessel was further washed with methanol (5 ml*2 times) and DMF (5 ml*2 times).

Step 11

Acetic anhydride (0.125 gm) was dissolved in dichloromethane (MDC) at 0-10° C. and charged into peptide vessel. The vessel was stirred for 3 hours and washed with dichloromethane (MDC-5 ml*4 times) and Methyltertiarybutylether (MTBE-5 ml*2 times) simultaneously.

Step 12

TFA (5 ml) was taken in RBF and cooled to 0-10° C. Above the resin bed was then charged into TFA solution. Reaction mixture was then stirred for 24 hrs. at room temperature. Solution was filtered and then washed with TFA (1 ml). Filtrate ml was then distilled out up to one volume under vacuum and below 35° C. Methyltertiarybutylether (MTBE) (30 ml) was taken in another RBF and cooled to 0-10° C. Residue was then charged in this solution and then stirred for 1 hr. and filtered. The compound was dried under vacuum at 35° C. for 6-8 hr. Purity of the crude was about 85%-95%. The compound was further purified using preparative HPLC to get highly pure compound, greater than about 85%-95%.

B. Preparation of Degarelix Acetate-Mannitol Premix

Two Different Strength Formulations were Prepared:

1. Degarelix Acetate-Mannitol Premix (80 mg)

a. Preparation of Sterile Mannitol 2.8 gm of Mannitol was dissolved in 19.6 ml milli Q water into RBF. Aseptic filtered this solution. 84 ml of Acetone was added into the above solution and stirred for 15 min, followed by filtering the reaction mass. The bed was washed with 5.6 ml acetone and the product was dried at 40 ° C. to yield a dry wt. of 2.4 to 2.6 gm.

b. Preparation of Sterile Degarelix Acetate 1.2 gm of Degarelix acetate was dissolved in 7.0 ml Acetic acid and 1.0 ml of methanol at 10-15° C. The reaction mass was stirred for 2 hours at 10-15° C. Aseptically filtered this solution and washed with 1.0 ml Acetic acid. Slowly above filtrate ml was added into precooled 40 ml MTBE at 10-15° C. The reaction mass was stirred for 30 min at 10-15° C., then filtered and washed with 2*5 ml MTBE solvent. The product was dried at 20 to 25° C. for 5 hrs. to yield a dry wt. 1.0 gm to 1.1 gm.

c. Mixing of Degarelix Acetate-Mannitol Premix 1.0 gm of Degarelix acetate (step b) was taken in 45 ml MTBE and 0.5 ml acetic acid at 20-30° C. 2.25 gm of mannitol (step a) was added into above solution with 5.0 ml MTBE. The reaction mass was stirred for 1 hr. at 20-30° C., filtered and washed with 2*5 ml MTBE. The product was dried under vacuum at 20-25° C. for 8 hrs. to yield a dry weight 3.0 to 3.25 gm.

2. Degarelix Acetate-Mannitol Premix (120 mg)

a. Preparation of Sterile Mannitol 2.8 gm of Mannitol was dissolved in 19.6 ml milli Q water into RBF. Aseptic filtered the solution. 84 ml of Acetone was added into the above solution and stirred for 15 min., then the reaction mass was filtered. The bed was washed with 5.6 ml acetone. The product was dried at 40° C. to yield a dry wt. of 2.4 to 2.6 gm.

b. Preparation of Sterile Degarelix Acetate 2.3 gm of Degarelix acetate was dissolved in 15.0 ml Acetic acid and 1.0 ml of methanol at 10-15° C. The reaction mass was stirred for 2 hours at 10-15° C. Aseptically filtered the above solution and washed with 1.0 ml Acetic acid. Slowly, the above filtrate ml was added into precooled 95 ml of MTBE at 10-15° C. The reaction mass was stirred for 30 min at 10-15° C., then filtered and washed with 2*5 ml MTBE solvent. The product was dried at 20 to 25° C. for 5 hrs. to yield a dry wt. 2.0 gm to 2.1 gm.

c. Mixing of Degarelix Acetate-Mannitol Premix 2.0 gm of Degarelix acetate (step b) was taken in 45 ml MTBE and 0.5 ml acetic acid at 20-30° C. 2.25 gm of mannitol (step a) was added into above solution with 5.0 ml of MTBE. The reaction mass was stirred for 1 hr. at 20-30° C., then filtered the and washed with 2*5 ml MTBE. The product was dried under vacuum at 20-25° C. for 8 hrs. to yield a dry weight 3.8 to 4.2 gm.

The following abbreviations are used herein unless expressly stated otherwise:

Fmoc-Rink amide AM-resin: (2',4'-Dimethoxyphenyl-Fmoc-aminomethyl)-phenoxyacetamidomethyl polystyrene resin Fmoc-D-Phe-(4Cl)-OH: 9-Fluorenylmethyloxycarbonyl-D-4-chlorophenylalanine Fmoc-D-2Nal-OH: 9-Fluorenylmethyloxycarbonyl-D-2-naphtylalanine Fmoc-D-3 Pal-OH: 9-Fluorenylmethyloxycarbonyl-D-3-pyridylalanine Fmoc-D-4Aph(tBuCbm)-OH: 9-Fluorenylmethyloxycarbonyl-N(4)-(t-butylcarbamoyl)-D-4-aminophenylalanine Fmoc-Aph(L-Hor)-OH: 9-Fluorenylmethyloxycarbonyl-N (4)-(L-hydroorotyl)-4-aminophenylalanine Fmoc-L-Leu-OH: 9-Fluorenylmethyloxycarbonyl-leucine-OH Fmoc-Ser(tBu)-OH: 9-Fluorenylmethyloxycarbonyl-O-t-butyl-serine Fmoc-Pro-OH: 9-Fluorenylmethyloxycarbonyl-L-proline
Fmoc-D-Ala-OH: 9-Fluorenylmethyloxycarbonyl-D-alanine
Fmoc-L-ILys(Boc)-OH: 9-Fluorenylmethyloxycarbonyl-N(s)-isopropyl-N(ε)-Boc-lysine
Fmoc-Rink amide-MBHA resin: 4-(2',4'-Dimethoxyphenyl-Fmoc-aminomethyl)-phenoxyacetamido-4-methylbenzhydrylamine polystyrene resin
Boc: tert-butyloxy-carbonyl
Fmoc: fluorenylmethyloxycarbonyl
HOBT: 1-Hydroxybenzotriazole While the foregoing has been described in some detail for purposes of clarity and understanding, it will be appreciated by one skilled in the art, from a reading of the disclosure, that various changes in form and detail can be made without departing from the true scope of the disclosure.

What is claimed is:

1. A method for preparing degarelix acetate mannitol sterile premix, comprising:
   providing a suitable resin;
   deprotecting the resin with a diethylenetriamine solution;
   reacting sequentially the deprotected resin with different Fmoc protected amino acids;
   deprotecting the amino acid in each sequence with a diethylenetriamine solution in a stepwise fashion to yield resin attached degarelix crude which is converted into resin attached crude degarelix acetate and then deprotected to yield crude degarelix acetate; and
   purifying the crude degarelix acetate to yield pharmaceutically acceptable degarelix acetate;
   dissolving the purified degarelix acetate in a suitable solvent;
   adding a mannitol solution to the degarelix acetate solution;
   aseptically filtering the mixture and adding an anti-solvent; and
   isolating therefrom degarelix-acetate mannitol sterile premix.

2. The method of claim 1, wherein the resin comprises Fmoc-Rink amide AM resin.

3. The method of claim 1, wherein the diethylenetriamine solution comprises 5% diethylenetriamine in DMF.

4. The method of claim 1, wherein the resin attached crude degarelix is converted into resin attached crude degarelix acetate in presence of acetic anhydride and dichloromethane (MDC).

5. The method of claim 1, wherein the resin attached crude degarelix acetate is deprotected using an acidic deprotecting agent to yield crude degarelix acetate, wherein the acidic deprotecting agent is at least one agent selected from a group consisting of tifluroacetic acid (TFA), hydrochloric acid (HC1), and methanesulfomc acid.

6. The method of claim 5, further comprising drying the crude degarelix acetate and wherein the crude degarelix acetate has a purity of at least 85%.

7. The method of claim 1, wherein the deprotected resin is reacted sequentially with different Fmoc protected amino acids using at least one condensing agent selected from a group consisting of N,Ndiisopropyl carbodiimide (DIPC), Benzotriazol-1-yloxy)tripyrrolidinophosphonium hexafluorophosphate (PyBOP), and N,N-dicyclohexyl carbodiimide (DCC).

8. The method of claim 1, wherein the Fmoc protected amino acids comprises a plurality selected from the group consisting of D-alanine, proline, lysine, leucine, 4-aminophenylaniline, 4-L-hyroortoyl-4-aminophenylalanine, t-butyl serine, 3-pyridylalanine, 4-chlorophenylalanine, 2-napthylalanine.

9. The method of claim 1, wherein the solvent comprises at least one of dimethyl sulfoxide (DMSO), dimethylformamide (DMF), dimethylacetamide (DMA) N-metyl pyrrolidone (NMP), and Dimethylformamide (DMF).

10. The method of claim 1, wherein the anti-solvent comprises at least one of acetone, methyl tert-butyl ether (MTBE), ethyl acetate, isobutyl acetate, isopropyl acetate, diisopropyl ether (DIPE), and tetrahydrofuran (THF).

* * * * *